United States Patent
Hansson (10) Patent No.: US 9,108,295 B2
(45) Date of Patent: Aug. 18, 2015

(54) BLASTING METALLIC IMPLANTS WITH TITANIUM OXIDE

(71) Applicant: Stig Hansson, Askim (SE)

(72) Inventor: Stig Hansson, Askim (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/719,895

(22) Filed: Dec. 19, 2012

(65) Prior Publication Data

US 2013/0165020 A1 Jun. 27, 2013

Related U.S. Application Data

(60) Provisional application No. 61/579,414, filed on Dec. 22, 2011.

(51) Int. Cl.
| | |
|---|---|
| *B24C 1/00* | (2006.01) |
| *B24C 1/06* | (2006.01) |
| *B24C 1/08* | (2006.01) |
| *A61L 27/04* | (2006.01) |
| *A61L 27/06* | (2006.01) |
| *A61L 27/50* | (2006.01) |

(Continued)

(52) U.S. Cl.
CPC .................. *B24C 1/00* (2013.01); *A61L 27/047* (2013.01); *A61L 27/06* (2013.01); *A61L 27/50* (2013.01); *B24C 1/06* (2013.01); *B24C 1/08* (2013.01); *A61C 2008/0046* (2013.01); *A61F 2/0077* (2013.01); *A61L 2400/18* (2013.01); *A61L 2430/12* (2013.01)

(58) Field of Classification Search
CPC .............. B24C 1/00; B24C 1/06; B24C 1/08; B24C 11/00; A61L 27/50; A61L 27/06; A61L 2400/18; A61C 2008/0046; A61F 2/0077
USPC .................................................. 451/38, 39, 40
See application file for complete search history.

(56) References Cited

U.S. PATENT DOCUMENTS

| | | | | |
|---|---|---|---|---|
| 5,667,385 | A | * | 9/1997 | Hansson ..................... 433/201.1 |
| 6,358,050 | B1 | * | 3/2002 | Bergstrom et al. ........... 433/173 |
| 8,277,577 | B2 | * | 10/2012 | Garcia Saban et al. ....... 148/281 |

(Continued)

FOREIGN PATENT DOCUMENTS

| | | |
|---|---|---|
| CN | 101604870 A | 12/2009 |
| DE | 102009016554 A1 | 9/2010 |

(Continued)

OTHER PUBLICATIONS

European Search Report, Application No. 11195289.1, Published Jun. 1, 2012.

(Continued)

*Primary Examiner* — Timothy V Eley
(74) *Attorney, Agent, or Firm* — David A. Zdurne; Douglas J. Hura; Leana Levin (57) ABSTRACT

A method of processing a surface of a metallic implant, such as a dental implant, to provide a desirable surface roughness, comprising subjecting the metallic implant to blasting with particles of one or more titanium oxides, including at least one non-stoichiometric titanium oxide, the particles having a compact morphology and a particle size in the range of from 1 to 300 µm. The resulting implant surface showed unexpectedly high retention strength after implantation in bone.

19 Claims, 7 Drawing Sheets

(51) Int. Cl.
   *A61C 8/00* (2006.01)
   *A61F 2/00* (2006.01)

(56) References Cited

U.S. PATENT DOCUMENTS

| | | | |
|---|---|---|---|
| 8,814,473 B2* | 8/2014 | Hatton et al. | 405/169 |
| 2003/0059742 A1 | 3/2003 | Webster et al. | |
| 2006/0161256 A1 | 7/2006 | Ziegler et al. | |
| 2007/0259427 A1 | 11/2007 | Storey et al. | |
| 2008/0135521 A1* | 6/2008 | Beaty | 216/109 |
| 2008/0269596 A1* | 10/2008 | Revie et al. | 600/424 |
| 2011/0196430 A1* | 8/2011 | Walsh et al. | 606/305 |
| 2013/0197660 A1* | 8/2013 | Bollati et al. | 623/23.57 |

FOREIGN PATENT DOCUMENTS

| | | | |
|---|---|---|---|
| WO | 9205745 | A1 | 4/1992 |
| WO | 9616611 | A1 | 6/1996 |
| WO | 2008078164 | A2 | 7/2008 |
| WO | 2009040124 | A1 | 4/2009 |

OTHER PUBLICATIONS

The International Journal of Oral & Marillofacial Implants, vol. 16, No. 2 (2001).

D.M. Esposito, Titanium in Medicine, Material Science, Surface Science, Engineering, Biological Resources & Medical Application; pp. 836-837, Springer-Veriag (2001).

Martin J Y et al, Clinical Oral Implants Resources, Mar 7(1), 27-37, 1996; Kieswetter K, et al., Journal Biomed Material Resource, Sep., 32(1), 55-63, 1996).

S. Hansson & M. Norton, Journal of Biomechanics 32(1999) 829-836.

N.N. Greenwood & A. Earnshaw, Chemistry of the Elements. Pergamon Press, 1984, ISBN 0-08-022056-8).

A. Wennerberg, T. Albreksson, & B. Andersson, Journal of Materials Science: Materials in Medicine, 6 (1995) 302-309.

A. Wennerberg, T. Albrektsson, C. Johansson & B. Andersson, Biomaterials 17 (1996) 15-22.

A. Wennerberg, T. Abreksson & J. Lausmaa, Journal of Biomedical Materials Research, 30(1996) 251-260.

* cited by examiner

Fig. 7c

BLASTING METALLIC IMPLANTS WITH TITANIUM OXIDE

CROSS-REFERENCE TO RELATED APPLICATIONS

This patent application claims the benefit of and priority to EP Application Ser No. 11195289.1, filed on Dec. 22, 2011 and U.S. Provisional Patent Application Ser. No. 61/579,414, filed on Dec. 22, 2011, which are herein incorporated by reference for all purposes.

FIELD OF THE INVENTION

The present invention relates to a method of producing a metallic implant intended for implantation into bone tissue.

TECHNICAL BACKGROUND

Dental implants are medical devices used to restore the function entailed with the loss of one or several teeth.

For implanting dental implants, which are generally metallic implants, into bone tissue, a one-stage procedure is nowadays often used. In this one-stage procedure, a first implant part, such as a dental fixture, is surgically placed into the bone tissue, and a healing abutment is then attached to the first implant part directly after the surgical operation. The soft tissue is then allowed to heal around the healing cap or the secondary implant part. When a healing cap is used, the cap is removed after a few weeks or months without any surgical procedure, and secondary implant parts, such as an abutment and a provisional crown, are attached to the first implant part. The one-stage procedure is for instance described in L Cooper et al: "A multicenter 12-month evaluation of single-tooth implants restored 3 weeks after 1-stage surgery", The International Journal of Oral & Maxillofacial Implants, Vol 16, No 2 (2001).

Earlier, a two-stage procedure has been used. The two-stage procedure, which in some cases still is preferable today, generally involves in a first stage surgically placing a first implant part, such as a dental fixture, into the bone tissue, where it is allowed to rest unloaded and submerged for a healing period, often of three months or more, in order to allow the bone tissue to grow onto the implant surface to permit the implant to be well attached to the bone tissue, the cut in the soft tissue covering the implant site being allowed to heal over the implant. In a second stage, the soft tissue covering the implant is opened and secondary implant parts, such as a dental abutment and/or a restoration tooth, are attached to the first implant part, such as said fixture, forming the final implant structure. This procedure is for instance described by Brånemark et al: "Osseointegrated Implants in the Treatment of the Edentulous Jaw, Experience from a 10-year period", Almquist & Wiksell International, Stockholm, Sweden. However, the fact that the implant not should be loaded during the healing period means that the secondary implant parts may not be attached to the first implant part and/or used during the healing period. In view of the discomfort associated with this, it is desirable to minimize the time period necessary for the above-mentioned first stage or even perform the entire implantation procedure in a single operation, i.e. to use the one-stage procedure.

For some patients, it might be considered better to wait at least three months before functionally loading the implant, both for one- and two-stage procedures. However, an alternative using the one-stage procedure is to put the implant in function directly after implantation (immediate loading) or a few weeks after implantation (early loading). These procedures are, for instance, described by D M Esposito, pp 836-837, in Titanium in Medicine, Material Science, Surface Science, Engineering, Biological Responses and Medical Application, Springer-Verlag (2001).

Hence, it is essential that the implant establishes a sufficient stability and bond between implant and bone tissue to enable the above disclosed immediate or early loading of the implant. It shall also be noted that an immediate or early loading of the implant may be beneficial to bone formation.

Two important factors for obtaining a high anchorage strength of the implant in bone are i) the chemical composition of the implant material and ii) the implant design at all length scales. The mechanisms of osseointegration of bone implants have been increasingly elucidated during the last 30 years and today bone implants are particularly designed with respect to material composition, shape and surface properties in order to promote osseointegration. For example, dental implants commonly used today are made of titanium or titanium alloys with a screw shaped design and a rough bone contact surface.

It is believed that an increased surface roughness, which gives a larger contact and attachment area between the implant and the bone tissue, provides a better mechanical retention and strength between implant and bone. Furthermore it is known that osteoblasts, i.e. bone-forming cells, sense and react to multiple chemical and physical features of the underlying surface. Topographical features on different length scales induce for example nucleation sites for collagen and minerals, cell attachment and biomechanical stimulation necessary to prevent bone resorption and eventually to gain bone. Therefore, the bone contact surface of bone implants is often provided with a microroughness, which has been demonstrated to affect cell proliferation and differentiation of osteoblast cells, and the local production of growth factors by the cells around a bone implant (Martin J Y et al, Clin Oral Implants Res, March 7(1), 27-37, 1996; Kieswetter K, et al., J Biomed Mater Res, September, 32(1), 55-63, 1996).

A mathematical model describing the relationship between surface roughness and interfacial shear strength was presented in S. Hansson and M. Norton, Journal of Biomechanics 32 (1999) 829-836.

Several methods have been proposed for processing metallic implants to provide a surface roughness. One commonly used method is blasting with alumina ($Al_2O_3$). However, a drawback of blasting with alumina particles is that some particles may remain on or partially embedded in the implant surface after blasting. Such contaminating blasting particles may impede the osseointegration of a titanium implant, and may also become detached after implantation, and may cause harm to the body. To avoid contamination remaining after a blasting process, various cleaning methods have been proposed, including cleaning with organic solvents, electropolishing, and treatment with alkaline or acidic solutions.

WO 92/05745 proposed an alternative method aiming to, in one operation, ensure that the surface of an implant is clean and that the surface has a macroscopic structure that favors a good retention of the implant in bone. The method involves blasting a titanium implant with particles of titanium oxide, preferably titanium dioxide. Since titanium dioxide is well tolerated and is in fact is also a constituent of the implant as such (titanium surfaces are naturally covered with a layer of titanium oxide), the blasting operation does not introduce any foreign, contaminating material onto the implant surface. Implants blasted according to the method of WO 92/05745 showed improved retention in bone 6 months after implantation, compared to non-blasted implants.

However, there remains a need for improved surface roughening methods to obtain the desired strong anchoring of the implant in bone, early after implantation. In particular it is desirable to enable or improve the outcome of early or immediate loading as described above.

SUMMARY OF THE INVENTION

It is an object of the present invention to provide improved surface roughening techniques and to further enhance osseointegration of implants intended for implantation into bone tissue.

According to a first aspect of the invention, this and other objects are achieved by a method of processing a surface of a metallic implant to provide a desirable surface roughness, i.e., a method of roughening the surface of a metallic implant, comprising subjecting the metallic implant to blasting with particles of one or more titanium oxides, including at least one non-stoichiometric titanium oxide, the particles having a compact morphology and a particle size in the range of from 1 to 300 μm. The blasting method resulted in unexpectedly high retention strength of the implant after only 4-11 weeks of implantation into bone, as measured by removal torque tests.

By "non-stoichiometric titanium oxide" means an oxide of titanium in which the Ti:O ratio is not 1:2. Accordingly, "stoichiometric titanium oxide" means titanium dioxide, $TiO_2$.

In some embodiments, the particles essentially consist of one or more titanium oxides.

In some embodiments, the particles comprise at least two titanium oxides.

In some embodiments, the particles may comprise more non-stoichiometric titanium oxide than stoichiometric titanium oxide. For example, a main portion of the titanium oxide(s) of the particles may be non-stoichiometric titanium oxide(s). By "main portion" is meant more than 50%. Hence, in some embodiments of the invention, the particles may comprise at least 50% by weight of non-stoichiometric titanium oxide, based on the total content of titanium oxide in the particles. In some embodiments, the particles may comprise at least 60%, at least 70%, or at least 80% by weight of non-stoichiometric titanium oxide, based on the total content of titanium oxide in the particles. Further, in some embodiments of the invention the particles have a weight ratio of non-stoichiometric titanium oxide to stoichiometric titanium oxide in the range of from 51:49 to 99:1, such as from 60:40 to 95:5, for example from 70:30 to 90:10.

In some embodiments, the at least one non-stoichiometric titanium oxide may be selected from among $Ti_2O_3$, $Ti_3O_4$, $Ti_6O_{11}$, $Ti_7O_{13}$, and $Ti_9O_{17}$. In some embodiments, the at least one non-stoichiometric titanium oxide may be selected from among $Ti_2O_3$, $Ti_3O_4$, $Ti_6O_{11}$, $Ti_7O_{13}$, $Ti_8O_{15}$, and $Ti_9O_{17}$.

In one embodiment, the particles may have a Vickers hardness in the range of from about 1000 to about 1200 $kgf/mm^2$, or from 980 to about 1100 $kgf/mm^2$.

In some embodiments, the particles have a size in the range of from 5 to 200 μm. For example, at least 90% by weight of the particles have a size in the range of from 6.8 (or about 7) to 125 μm, and typically from 6.8 (or about 7) to 90 μm. In some embodiments, at least 95% of the particles have a size in the range of from 6.8 (or about 7) to 125 μm, and typically from 6.8 (or about 7) to 90 μm. In other embodiments at least 90% by weight of the particles have a size in the range of from 90 to 180 μm.

The particles used in a method according to embodiments of the invention may have an irregular morphology. However, a majority of the particles are typically non-elongated.

In embodiments of the invention, the implant may comprise titanium or an alloy thereof. Since titanium exposed to air has a chemically resistant layer of oxide, the blasting operation will not introduce any foreign, contaminating material onto the implant. The implant is typically a bone implant (i.e., an implant intended for implantation into bone tissue), for example a dental implant.

The method typically includes the steps of providing a metallic implant having a surface; and blasting at least part of the surface of the metallic implant with the particles described above.

It is noted that the invention relates to all possible combinations of features recited in the claims.

DETAILED DESCRIPTION OF THE INVENTION

Following the insight that titanium oxide was suitable as a blasting material and may provide acceptable surfaces, extensive work has been put into realizing this finding, and developing a blasting process that provides further improved results. Surprisingly, it was found that blasting a metallic implant, in particular a titanium implant, with a blasting powder consisting of particles of titanium oxide having specific properties yields a highly desirable result, as evidenced by removal torque tests of implanted fixtures.

As used herein the term "implant" includes within its scope any device of which at least a part is intended to be implanted into the body of a vertebrate animal, in particular a mammal, such as a human. Implants may be used to replace anatomy and/or restore any function of the body.

"Bone implant" refers to an implant intended for implantation, at least partially, into bone tissue.

Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

The implant treated by the method of the invention is a bone implant and may be a dental implant, such as a fixture, an abutment, or combinations thereof, such as a one-piece implant. The implant may also be an orthopaedic implant, such as a hip joint component intended for implantation into the neck of the femur of a patient.

The implant to be treated with the method of the invention may consist of any suitable metal, e.g. titanium or an alloy thereof, zirconium or an alloy thereof, hafnium or an alloy thereof, niobium or an alloy thereof, tantalum or an alloy thereof, a chromium-vanadium alloy or any combination of these materials. It may be noted that in contact with oxygen (e.g. air), titanium, zirconium, hafnium, tantalum, niobium and their alloys are instantaneously covered with a thin oxide layer, referred to as native oxide layer. The native oxide layer present on the surface of titanium bodies mainly consists of titanium(IV) dioxide ($TiO_2$) with minor amounts of $Ti_2O_3$, TiO and $Ti_3O_4$.

Alternatively, the implant may comprise a non-metallic body or core provided with a metallic layer, e.g. an applied titanium layer, for example an applied metallic surface layer covering a non-metallic body or a body partly consisting of a non-metallic material. Examples of non-metallic materials comprise a ceramic, a plastic and a composite material.

The method of the invention involves blasting the surface of a medical implant, for example a dental implant, with a blasting powder comprising particles of titanium oxide.

Figure 1:
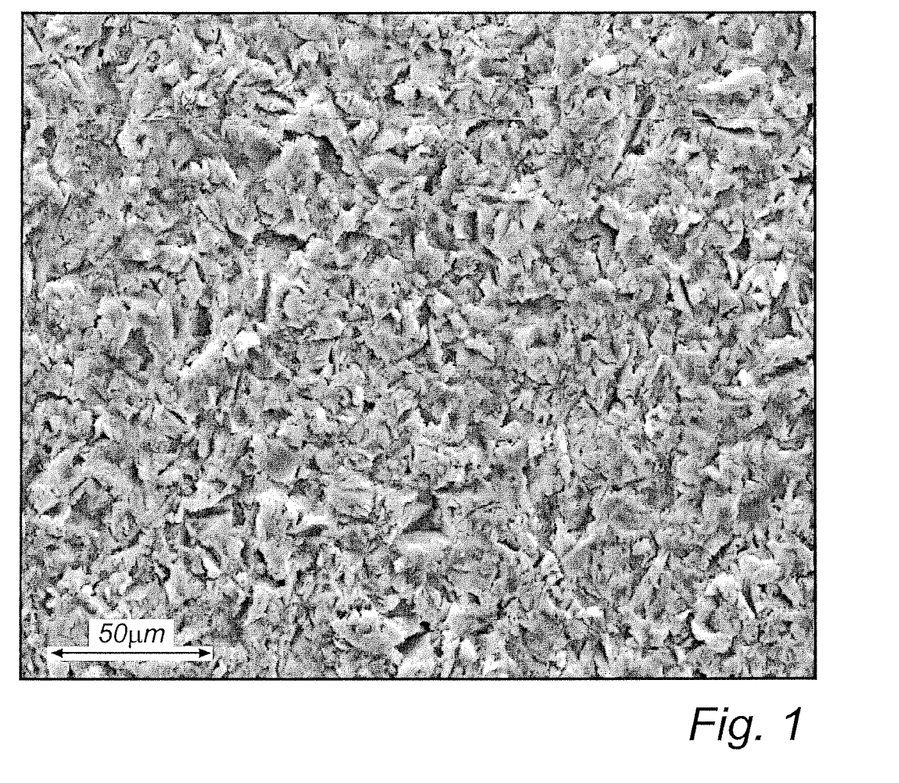
FIG. 1 is a scanning electron microscopy (SEM) image of a titanium implant surface processed according to embodiments of the invention.
Figure 2:
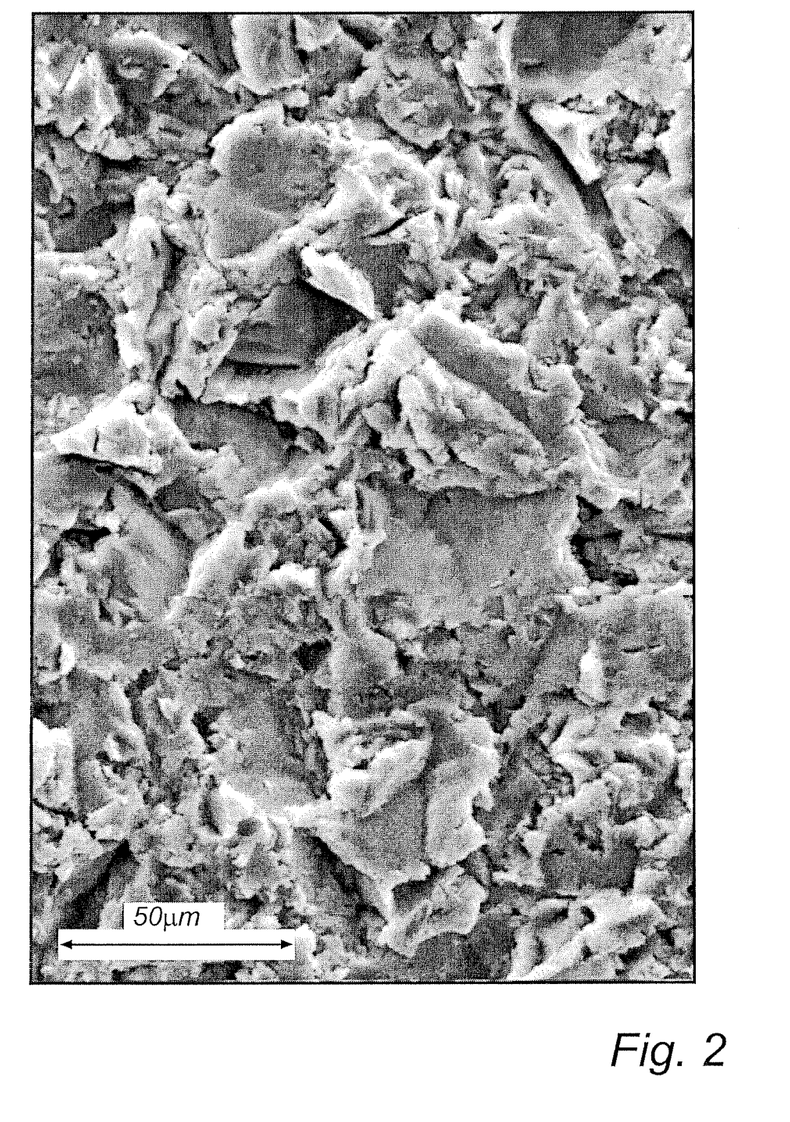
FIG. 2 is a scanning electron microscopy (SEM) image of another titanium implant surface processed according to embodiments of the invention.

FIGS. 1 and 2 are SEM images showing surfaces processed according to embodiments of the invention. The surface of FIG. 1 is a titanium surface which has been subjected to blasting with relatively fine particles of titanium oxide (at least 90% of the particles having a size in the range of from about 7 to 90 μm). FIG. 2 shows a titanium surface which has been subjected to blasting with relatively coarse particles of titanium oxide (at least 90% of the particles having a size in the range of from 90 to 180 μm).

The particles used for blasting according to the present method generally have a particle size in the range of from 1 to 300 μm, more often from 5 to 200 μm. For example, at least 90% by weight of the particles may have a particle size in the range of from 90 to 180 μm. In one embodiment, e.g. at least 95%, and more typically at least 99% by weight of the particles have a size in the range of from 106 to 180 μm.

In other embodiments, at least 90% by weight of the particles may have a size in the range of from about 5 to 125 μm, or about 7 to 125 μm. For example, in one embodiment, at least 50% by weight of the particles may have a size in the range of from of 45 to 90 μm.

It has been found that these sizes may be advantageous, in particular in combination with the morphology and chemical composition and/or hardness characteristics described below, in that they may yield a highly desirable surface roughness on the surface of a metallic body intended for implantation into bone tissue, for example a titanium implant intended for implantation into the jawbone. The smaller blasting particles may also be particularly useful for blasting a threaded fixture.

Smaller blasting particles typically yield smaller surface irregularities than larger particles, and the size of the irregularities is normally smaller than the size of the particles.

Complete blasting of a titanium surface using blasting particles having a size of 5-200 μm may result in a size of the irregularities on the surface in the range 1 to 50 μm. By "complete blasting" is meant that there are no unaffected areas, such that the entire area of a blasted surface or surface portion has been impacted by the blasting particles. This is the case for the blasted surfaces shown in FIGS. 1 and 2. As can be seen, the surface irregularities have sizes in the range from about one or a few micrometers and at least up to about 50 μm. The variation in surface irregularities may be due, in part, to a size distribution of the blasting particles, but also in part to the fact that the impact area of a second blasting particle may partially overlap with that produced by a first particle, such that irregularities of different shapes and sizes are produced.

Furthermore, it has been found that the morphology of the particles also affects the shape and size of the surface roughness resulting from the blasting operation. The particles used in the present invention typically have an irregular shape, which may differ somewhat between individual particles, but which is however generally particular or compact rather than elongated, at least for a majority of the particles.

Figure 3A:
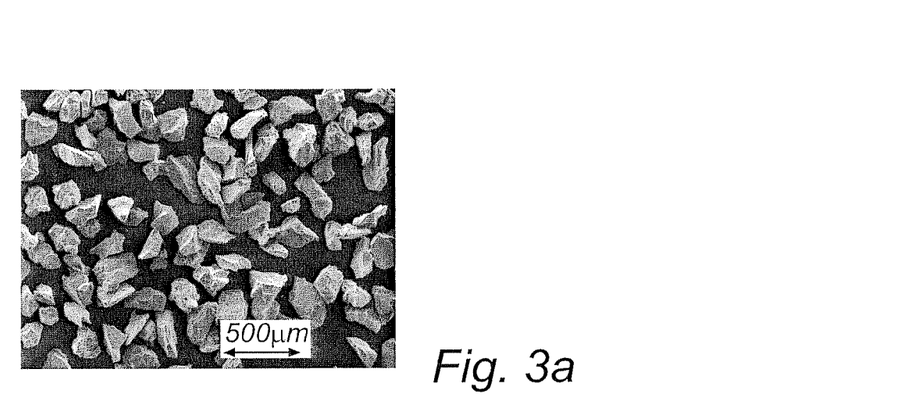
FIG. 3a-c are SEM images, at different magnifications, showing coarse blasting particles used in embodiments of the invention.
Figure 3B:
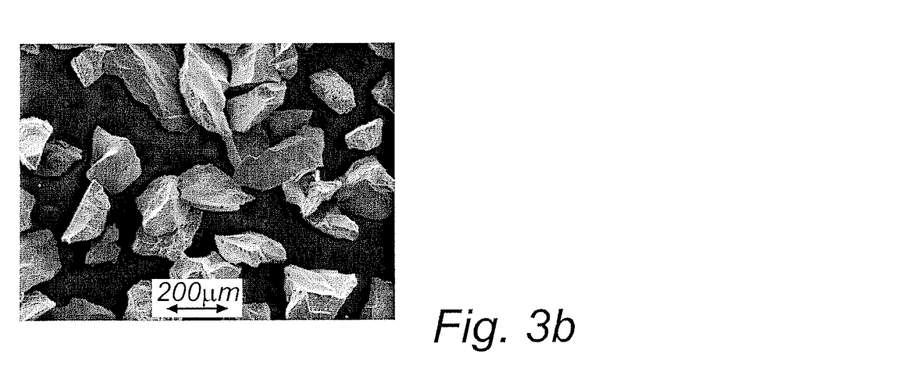
Figure 3C:
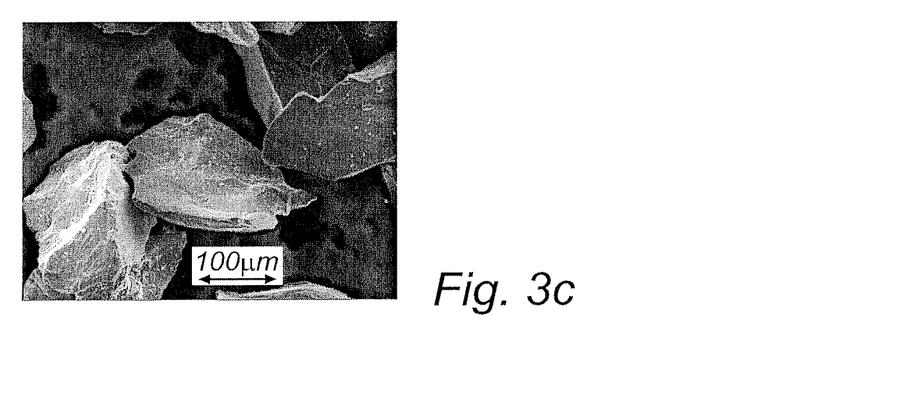
Figure 4A:
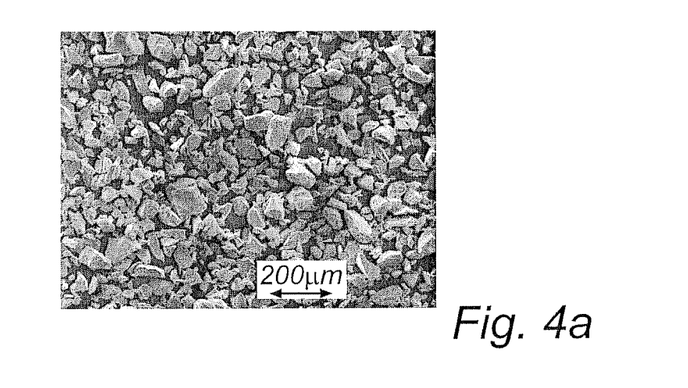
FIG. 4a-c are SEM images, at different magnifications, showing fine blasting particles used in embodiments of the invention.
Figure 4B:
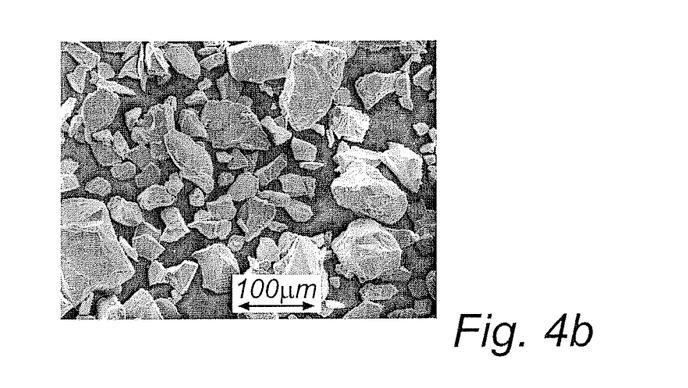
Figure 4C:
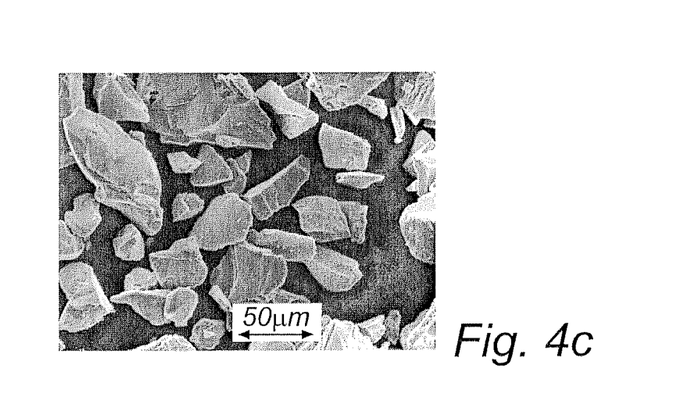

FIGS. 3a-b and 4a-c show SEM images of blasting powders that may be used in embodiments of the present inventions. FIG. 3a-c show, at different magnifications, blasting particles, of which at least 90% by weight have a size in the range of from 90 to 180 μm (also referred to as "coarse blasting particles" or "coarse blasting powder" in the context of the present invention). The scale bar represents 500 μm (FIG. 3a), 200 μm (FIG. 3b) or 100 μm (FIG. 3c). FIG. 4a-c show, at different magnifications, blasting particles, of which at least 90% by weight have a size in the range of from about 7 to 90 μm (also referred to as "fine blasting particles" or "fine blasting powder" in the context of the present invention). The scale bar represents 200 μm (FIG. 4a), 100 μm (FIG. 4b) or 50 μm (FIG. 4c).

As can be seen in these figures, the majority of the particles have an irregular, even angular or flake-like, shape which is however generally compact, rather than elongated. In fact, it was found that elongated, (rod-shaped or needle-shaped) particles did not yield a satisfactory surface roughness.

The particles used in the invention are generally very pure, and may consist essentially of titanium oxide, comprising only very minor amounts (e.g., 1.5% by weight or less) of other matters, such as other metal oxides. In this context, "essentially" means that the particles may contain up to 3% by weight material other than titanium oxide.

As used herein, the expression "titanium oxide" is intended to encompass one or more oxide of titanium, in particular crystalline forms, including for example TiO, $TiO_2$, $Ti_2O_3$, $Ti_3O_4$, $Ti_6O_{11}$, $Ti_7O_{13}$, and/or $Ti_9O_{17}$. Another crystalline form of titanium oxide is $Ti_8O_{15}$. Where particularly TiO is intended, it is here referred to as "titanium monooxide". Hence, "one or more titanium oxides" means at least one titanium oxide, which may be any one of the known oxide forms of titanium.

Titanium dioxide, i.e. titanium(IV) oxide, is the most stable oxide of titanium, and is referred to as a stoichiometric oxide. Hence, a non-stoichiometric titanium oxide means an oxide of titanium in which the Ti:O ratio is not 1:2. Non-stoichiometric titanium oxides include $Ti_2O_3$, $T_3O_5$, $Ti_6O_{11}$, the Magneli-type phases $Ti_nO_{2n-1}$, n being from 4 to 9, such as $Ti_7O_{13}$ and $Ti_9O_{17}$, and also $TiO_x$, 0.70≤x≤1.30. (N. N Greenwood and A. Earnshaw, *Chemistry of the elements*. Pergamon Press, 1984, ISBN 0-08-022056-8).

In embodiments of the invention, the blasting particles comprise at least one non-stoichiometric titanium oxide. For example the particles may comprise one or more of $Ti_5O_{11}$, $Ti_7O_{13}$, and/or $Ti_9O_{17}$, and/or $Ti_8O_{15}$. However the particles additionally also comprise stoichiometric titanium oxide, i.e. $TiO_2$, to some extent. Crystalline forms of titanium oxide present in the particles used in embodiments of the invention may thus include $TiO_2$ (typically rutile and/or anatase), $Ti_2O_3$, $Ti_3O_4$, $Ti_6O_{11}$, $Ti_7O_{13}$, and/or $Ti_9O_{17}$, and/or $Ti_8O_{15}$.

In embodiments of the invention, the particles may comprise more non-stoichiometric titanium oxide than stoichiometric titanium oxide. For example, a main portion of the titanium oxide(s) of the particles may be non-stoichiometric titanium oxide(s). By "main portion" is meant more than 50%. Hence, in some embodiments of the invention, the particles may comprise more than 50% by weight of non-stoichiometric titanium oxide, based on the total content of titanium oxide in the particles. In some embodiments, the particles may comprise at least 60%, at least 70% or at least 80% by weight of non-stoichiometric titanium oxide, based on the total content of titanium oxide in the particles. Typically however there may also be a small content of stoichiometric titanium oxide (titanium dioxide in the form of rutile and/or anatase) for example at least 1% by weight, at least 5% by weight or at least 10% by weight. Typically the content of stoichiometric titanium oxide is less than 50% by weight, e.g. 40% by weight or less, such as 30% by weight or less. In some embodiments, the content of stoichiometric titanium oxide, in relation to the total content of titanium oxide, may be about 20% by weight.

In embodiments of the invention the particles may have a weight content of non-stoichiometric titanium, in relation to the total content of titanium oxide, in the range of from 50 to 99% by weight, for example from 50 to 95% by weight, for example from 50 to 90% by weight, such as from 60 to 90% by weight or from 70 to 90% by weight. In some embodiments, the weight ratio of non-stoichiometric titanium oxide to stoichiometric titanium oxide may be about 80:20.

The weight content of stoichiometric and non-stoichiometric oxide, respectively, may be estimated based on an X-ray diffraction (XRD) spectrum.

Figure 5A:
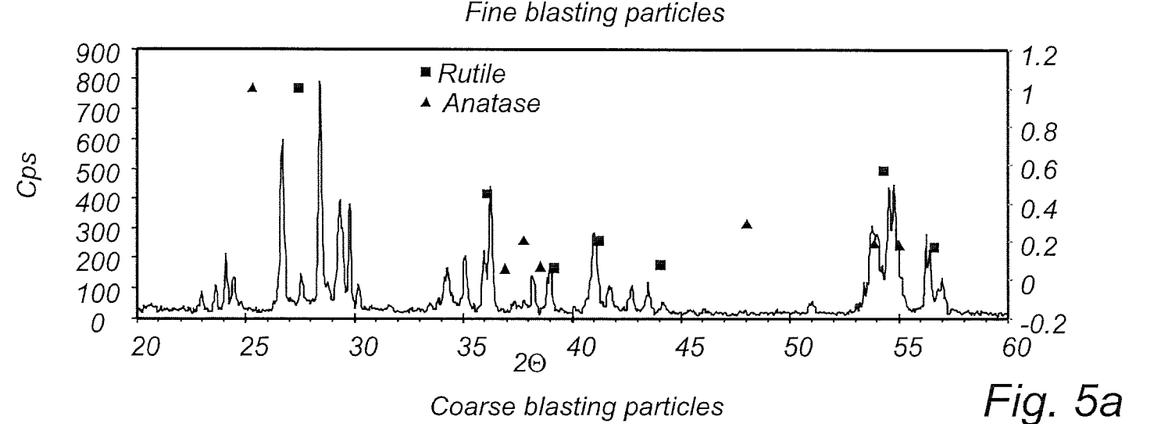
FIG. 5a-b show X-ray diffraction spectra for fine and coarse blasting particles, respectively, used in embodiments of the invention.
Figure 5B:
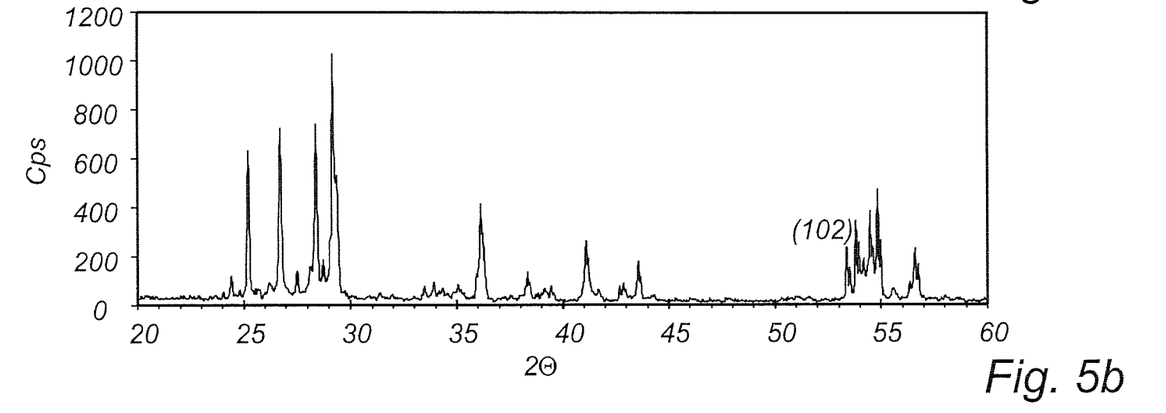

X-ray diffraction spectra showing the composition of a fine blasting powder and a coarse blasting powder are presented, respectively, in FIG. 5a and FIG. 5b.

Figure 7A:
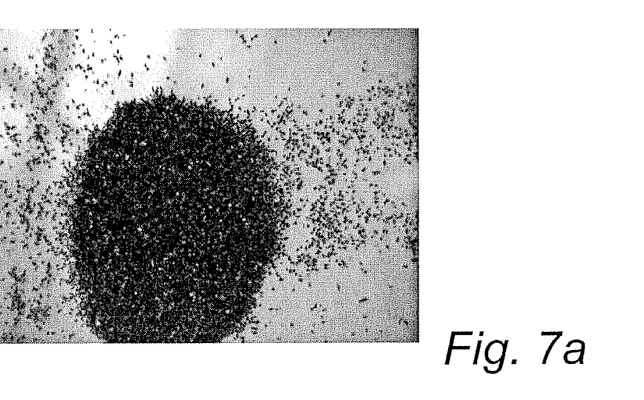
FIG. 7a-c are photographs showing a darkly colored blasting powder of particles as used in embodiments of the invention and a white powder of titanium dioxide particles, respectively.
Figure 7B:
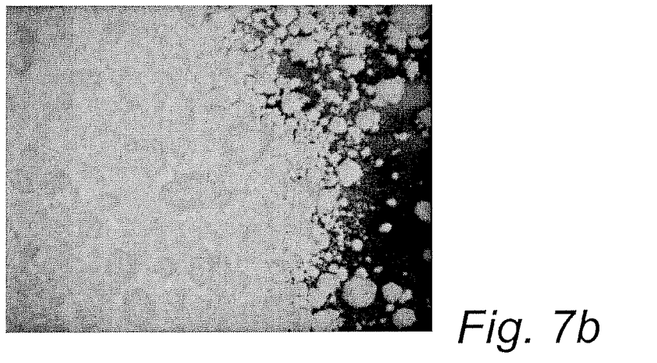
Figure 7C:
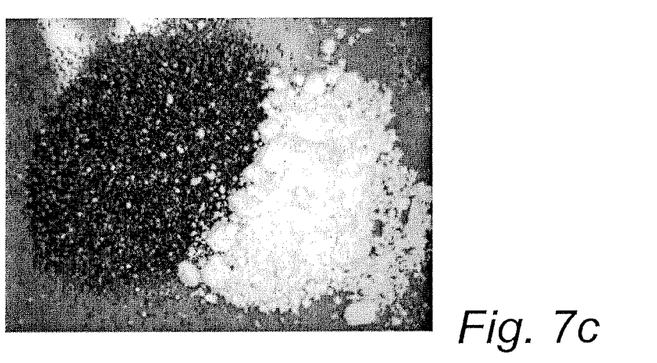

Furthermore, as can be seen in FIG. 3a-c and FIG. 4a-c, and perhaps even more clearly in FIG. 7a, the particles used in the present invention have a dark color (grey or black). This dark color may be explained by a disturbed crystal lattice, which thus may indicate the presence of one or more non-stoichiometric oxides which interrupt e.g. a $TiO_2$ crystal lattice. The particles are typically dense, i.e. non-porous. For comparison, FIG. 7b shows a titanium dioxide powder, which is white. FIG. 7c shows a dark, at least partially non-stoichiometric titanium oxide blasting powder as used in the invention, next to a stoichiometric, white titanium dioxide powder.

In some embodiments of the invention, the particles used may have a hardness that is higher than the hardness of pure rutile $TiO_2$ (it is noted that rutile is harder than anatase). The particles may have a Vickers hardness ($VH_{100}$) of at least about 1000, such as 980. For example, the particles may have a Vicker's hardness in the range of from 900 or typically from about 1000 and up to 2500, up to 2000, up to 1500, or up to 1200.

In one example embodiment the particles had a Vickers hardness in the range of from 980 to about 1100 (see Example 1 below). Table 1 presents the hardness of various blasting materials: particles according to an example embodiment of the invention, $TiO_2$ and corundum.

TABLE 1

| Material | Vickers hardness ($VHN_{100}$, $kgf/mm^2$) |
|---|---|
| Particles according to an example embodiment of the invention | about 980-1100 |
| Rutile ($TiO_2$) | 894-974 |
| Corundum ($Al_2O_3$) | >2600 |

It is believed that the hardness of the blasting particles may contribute to the advantageous blasting result. It is also believed that the hardness is at least in part due to the chemical composition.

The particles used in the invention may be so-called fused and crushed particles, meaning that they are produced by fusing to form a large body of titanium oxide and subsequently crushing the large body to form the final particles. Such methods are generally known, and are typically used for producing titanium oxide powder for thermal spray coatings for applications such as thermal insulation and corrosion resistance. Surprisingly, the present inventor found that particles produced by this method yield excellent results when used for blasting metallic implants.

For example, the particles used in the present invention may be produced from crude titanium oxide which is purified via conversion to titanium tetrachloride. In such a process, the starting material is reduced with carbon, oxidized with chlorine to give titanium tetrachloride (carbothermal chlorination). The titanium tetrachloride, which is a dense, colorless liquid, is distilled, re-oxidized in a pure oxygen flame or plasma at a temperature of 1500-2000 K to yield pure titanium oxide. The product is subsequently fused and crushed to provide the desirable particles size.

A blasting method according to the invention involves providing a metallic body intended as an implant, and blasting at least part of a surface of the metallic body. The surface of the metallic body may typically comprise a thin layer of native metal oxide, such as native titanium oxide in the case of a titanium body.

The blasting process may be performed using conventional equipment. The implant to be blasted may be rotated during the blasting operation, such that more than one side of the implant is subjected to the blasting treatment. The blasting operation may be performed on part of the implant surface or on the whole implant surface.

The implant may be subjected to any kind of pretreatment in order to create a desired substrate surface for further modification according to the inventive method. For example, the implant may be pretreated by a mechanical, chemical or thermal treatment, or any combination thereof, to obtain desired initial surface characteristics. A chemical treatment may for instance comprise a cleaning or degreasing process.

Following the blasting treatment of the invention, the implant may optionally be subjected to further surface treatment to provide additional surface modification, e.g. to provide a finer surface roughness, for example by acid etching.

EXAMPLES

Example 1

Characterization of Blasting Particles (a) X-Ray Diffraction (XRD)

Coarse and fine blasting powders, respectively, as described above were subjected to XRD analysis. XRD is a rapid and non-destructive technique for analyzing chemical composition and crystallographic structure of materials.

The XRD spectra are presented in FIGS. 5a and 5b, respectively. Reference peaks for rutile and anatase (both $TiO_2$) are included. It can be concluded from the spectra that the particles contain non-stoichiometric titanium oxides of different composition. Further, judging from the number of peaks that do not represent rutile or anatase (i.e., $TiO_2$) compared with the number of peaks that do represent rutile or anatase, it may be concluded that a considerable portion, and even the main part, of the titanium oxide of the blasting particles is formed of non-stoichiometric titanium oxides.

(b) Hardness Determination

Three samples were produced by mixing the titanium oxide particles with a polymer resin which was hardened. The samples were ground and polished to provide a planar measuring surface (see FIG. 6).

The hardness was measured with a Matsuzama MTX50 micro hardness tester. The Vickers hardness method uses a pyramidal diamond indenter which is applied on a sample surface with a specific load. The facing angle of the indenter is 136°. The hardness is related to the size of the resulting indent and calculated according to the following equations:

$$A = \frac{d^2}{2\sin\frac{\theta}{2}} \approx \frac{d^2}{1.854}$$

$$HV = \frac{F}{A} \approx \frac{1.854F}{d^2}$$

where
A is the surface area of the indentation (mm$^2$);
d is the diagonal length of the indentation (mm);
$\theta$ is the facing plane angle of pyramidal diamond indenter (°), i.e. 136°;
F is the test load (kgf, kilogram-force, also referred to as kp, kilopond); and HV means Vickers hardness.

Figure 6:
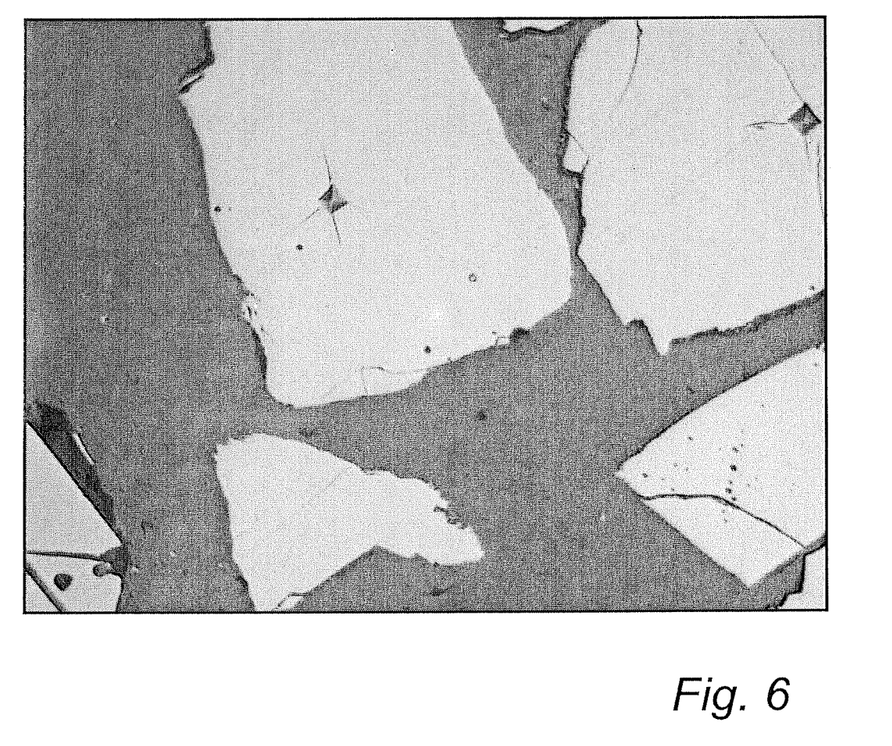
FIG. 6 is an image of polished blasting particles which have been subjected to hardness measurement.

The load of the hardness tester was set to 100 g. Measurements were made on 7 separate particles (one indent on each particle). Each indent was measured twice. FIG. 6 shows an image of the polished particles after indentation.

The average hardness was about 1040, with a standard deviation of 45, see Table 2 below.

TABLE 2

| Particle No. | Vickers hardness (HV$_{100}$, kgf/mm$^2$) |
|---|---|
| 1 | 1097.2 |
|   | 1080.5 |
| 2 | 1056.2 |
|   | 1048.3 |
| 3 | 995.2 |
|   | 1002.5 |
| 4 | 988.0 |
|   | 980.8 |
| 5 | 1010.0 |
|   | 980.8 |
| 6 | 1056.2 |
|   | 1097.2 |
| 7 | 1097.2 |
|   | 1048.3 |
| Average | 1038 |
| Std dev | 45 |

Example 2

Blasting Operation

Titanium fixtures were thoroughly cleaned and degreased according to conventional methods. The fixtures were subjected to blasting with fine or coarse blasting particles as defined herein. Air was used as the carrying medium. Each fixture was rotated to expose all sides.

Example 3

Characterization of a Blasted Implant Surface a) SEM

Blasted surfaces (titanium fixtures) were examined using scanning electron microscopy (SEM). Images are presented in FIGS. 1 and 2. The scale bar represents 50 µm.

Topographical evaluation was also performed on fine-blasted and coarse-blasted surfaces, respectively, using SEM. Topographical data of the resulting surfaces are presented in Table 3. "Fine" refer to blasting particles of which 90% have a size in the range of from about 7 to 90 µm. "Coarse" refers to blasting particles of which 90% have a size in the range of from 90 to 180 µm.

TABLE 3

| Type of blasting particles used | S$_a$ (µm) | S$_{sk}$ | S$_{dr}$ (%) | S$_{dq}$ | S$_{ds}$ (µm$^{-2}$) |
|---|---|---|---|---|---|
| Fine | 0.88 ± 0.18 | — | 38.10 ± 21.68 | — | 0.081 ± 0.02 |
| Fine | 0.91 ± 0.13 | 0.39 (2.20) | 39.14 ± 9.77 | 1.97 ± 0.68 | 0.16 ± <0.01 |
| Coarse | 1.54 ± 0.17 | 0.21 ± 0.87 | 80.23 ± 26.50 | 3.51 ± 1.18 | 0.15 ± 0.01 |

Example 4

Effect of Blasted Implants

Screw-shaped implants (fixtures) of commercially pure (c. p.) titanium were used. 24 implants were only machined ("machined implants") and 24 implants were machined and subsequently blasted using coarse blasting particles as described above ("blasted implants"). Two machined and two blasted implants were implanted in each proximal tibial methaphysis of mature New Zealand white (NZW) rabbits. A total of 12 rabbits were used. The retention strength was evaluated using removal torque tests on two implants from each group (machined and blasted) after 2, 4, 7, 9 and 11 weeks, respectively. The results are presented in Table 4.

TABLE 4

| Weeks after implantation | Removal torque (Ncm), machined implants (average of two implants) | Removal torque (Ncm), blasted implants (average of two implants) |
|---|---|---|
| 2 | 8 | 8.5 |
| 4 | 19.5 | 55.4 |
| 7 | 15.5 | 58 |
| 9 | 25 | 79.5 |
| 11 | 22 | 88 |

These results may be compared with previously published studies investigating the retention strength by removal torque tests, using the same type of threaded implants and surgical evaluation. In one study [A Wennerberg, T Albrektsson, C Johansson and B Andersson, *Biomaterials* 17 (1996) 15-22] it was found that implants of c. p. titanium blasted with either 25 μm sized $Al_2O_3$ particles or 25 μm sized $TiO_2$ particles, respectively, resulted in removal torque values of only about 25 Ncm after 12 weeks of implantation in rabbit tibia. In another study [A Wennerberg, T Albreksson, and B Andersson, Journal of Materials Science: Materials in Medicine, 6 (1995) 302-309] using identical methods, implants of c. p. titanium blasted with either 25 μm sized $Al_2O_3$ particles or 25 μm sized $TiO_2$ particles, respectively, both resulted in average removal torque values of about 42-45 Ncm after 12 weeks of implantation in rabbit tibia (the maximum value for $TiO_2$ blasted implants was 66 Ncm). Moreover, a surface blasted with 250 μm sized particles of $Al_2O_3$ was also evaluated, and showed no improvement over the surface blasted with 25 μm sized particles (Wennerberg et al, 1995).

In yet another comparable study [A Wennerberg, T Albreksson and J Lausmaa, *Journal of Biomedical Materials Research*, 30 (1996) 251-260] using identical methods, implants blasted with 25 μm $Al_2O_3$ particles showed a removal torque value of about 40-45 Ncm (average) after 12 weeks of implantation in NZW rabbit tibia.

Thus, considering the results previously obtained by blasting with substantially pure $TiO_2$, the present method which uses blasting particles comprising at least one non-stoichiometric titanium oxide and having the size distribution described above, yields unexpectedly favorable results in terms of removal torque values after only 4-11 weeks of implantation.

The person skilled in the art realizes that the present invention by no means is limited to the embodiments described above. On the contrary, many modifications and variations are possible within the scope of the appended claims.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

What is claimed is:

1. A method of processing a surface of a metallic implant to provide a desirable surface roughness, comprising the step of subjecting the metallic implant to blasting with particles of one or more types of titanium oxides, including at least one type of a non-stoichiometric titanium oxide, said particles having a compact morphology and a particle size in the range of from 1 to 300 μm.

2. The method according to claim 1, wherein the particles essentially consist of one or more types of titanium oxides.

3. The method according to claim 1, wherein the particles comprise at least two types of titanium oxides.

4. The method according to claim 1, wherein a main portion of the particles of the one or more types of titanium oxides is particles of a non-stoichiometric titanium oxide.

5. The method according to claim 1, wherein the particles have a weight ratio of non-stoichiometric titanium oxide particles to stoichiometric titanium oxide particles in the range of from 51:49 to 99:1.

6. The method according to claim 1, wherein the at least one non-stoichiometric titanium oxide particles is selected from the group consisting of $Ti_2O_3$, $Ti_3O_4$, $Ti_6O_{11}$, $Ti_7O_{13}$, and $Ti_9O_{17}$.

7. The method according to claim 1, wherein the particles have a Vickers hardness in the range of from about 1000 to about 1200 $kgf/mm^2$.

8. The method according to claim 1, wherein the particles have a Vickers hardness in the range of from 980 to about 1100 $kgf/mm^2$.

9. The method according to claim 1, wherein the particles have a size in the range of from 5 to 200 μm.

10. The method according to claim 1, wherein at least 90% by weight of the particles have a size in the range of from 6.8 to 125 μm.

11. The method according to claim 10, wherein at least 95% of the particles have a size in the range of from 6.8 to 125 μm.

12. The method according to claim 1, wherein at least 90% by weight of the particles have a size in the range of from 90 to 180 μm.

13. The method according to claim 1, wherein the particles have an irregular morphology.

14. The method according to claim 1, wherein a majority of the particles are non-elongated.

15. The method according to claim 1, wherein the implant comprises a metal selected from the group consisting of titanium, titanium alloy, zirconium, zirconium alloy, hafnium, hafnium alloy, niobium, niobium alloy, tantalum, tantalum alloy, a chromium-vanadium alloy and any combination thereof.

16. The method according to claim 1, wherein the implant is a dental implant.

17. The method according to claim 1, comprising the steps of providing a metallic implant having a surface; and blasting at least part of the surface of the metallic implant with said particles.

18. The method according to claim 1, wherein: (i) the particles have a weight ratio of non-stoichiometric titanium oxide particles to stoichiometric titanium oxide particles in the range of from 60:40 to 95:5; and (ii) at least 90% by weight of the particles have a size in the range of from 6.8 to 90 μm.

19. The method according to claim 1, wherein: (i) the particles have a weight ratio of non-stoichiometric titanium oxide particles to stoichiometric titanium oxide particles in the range of from 70:30 to 90:10; and (ii) at least 95% of the particles have a size in the range of from 6.8 to 90 μm.

* * * * *